United States Patent [19]

Akhavi

[11] 4,240,428
[45] Dec. 23, 1980

[54] SEGMENTED SYRINGE LOCKING SLEEVE

[75] Inventor: David S. Akhavi, Los Angeles, Calif.

[73] Assignee: American Hospital Supply Corporation, Evanston, Ill.

[21] Appl. No.: 953,689

[22] Filed: Oct. 23, 1978

[51] Int. Cl.³ .............................................. A61M 5/00
[52] U.S. Cl. .............................................. 128/218 R
[58] Field of Search ............... 128/218 R, 218 N, 215, 128/216, 221, 247

[56] References Cited

U.S. PATENT DOCUMENTS

| | | | |
|---|---|---|---|
| 3,306,291 | 2/1967 | Burke | 128/221 X |
| 3,542,024 | 11/1970 | Burke | 128/221 |
| 3,728,184 | 4/1973 | Burke et al. | 156/73 |
| 4,027,669 | 6/1977 | Johnston et al. | 128/218 N |

FOREIGN PATENT DOCUMENTS 1086763  5/1965  United Kingdom ............... 128/221

*Primary Examiner*—John D. Yasko
*Attorney, Agent, or Firm*—Larry N. Barger

[57] ABSTRACT

A hypodermic syringe with a thermoplastic syringe barrel having an integral locking sleeve at its forward end. The locking sleeve has a slot construction positioned relative to the barrel's front end to enhance mold release flexing of the sleeve during formation and firm locking control on a hypodermic needle or the like during use.

7 Claims, 3 Drawing Figures

SEGMENTED SYRINGE LOCKING SLEEVE

BACKGROUND

U.S. Pat. No. 4,027,669 describes a thermoplastic syringe barrel with an integrally molded internally threaded locking sleeve at its forward end. The locking sleeve was segmented by three circumferentially spaced slots to provide a sleeve structure with internal threads that could be longitudinally stripped (without unscrewing) from its mold during formation.

During mold stripping, it is desirable to have the sleeve as flexible as possible so the threads are not damaged during the stripping process. During use, just the opposite is desirable, i.e. the sleeve should be as stiff as possible to prevent lateral ears of a hypodermic needle from slipping on the threads. Because of these two divergent needs relative to flexibility of the sleeve, seemingly minute changes in structure can have a tremendous effect on moldability and performance of the syringe. It was previously believed necessary to include a circumferentially uninterrupted portion of approximately 0.100 inch length at a rear of the locking sleeve. This was felt necessary to provide the backup support to prevent overflexing of the sleeve when the needle ears were pushing outwardly against the sleeve during use. An expanded view of this prior art is shown in FIG. 1.

SUMMARY OF THE INVENTION

In the present invention, the applicant unexpectedly found substantially better performance in (1) reduction in mold cycle time, (2) strip ejection and thread profile, and (3) syringe needle holding power when the uninterrupted support ring at the base of the prior art locking sleeve was substantially reduced from 0.100 inch or eliminated, and a ribbed wall of the sleeve had a wall thickness (excluding ribs) of from 0.030 to 0.045 inch.

THE DRAWINGS

DETAILED DESCRIPTION

Figure 1:
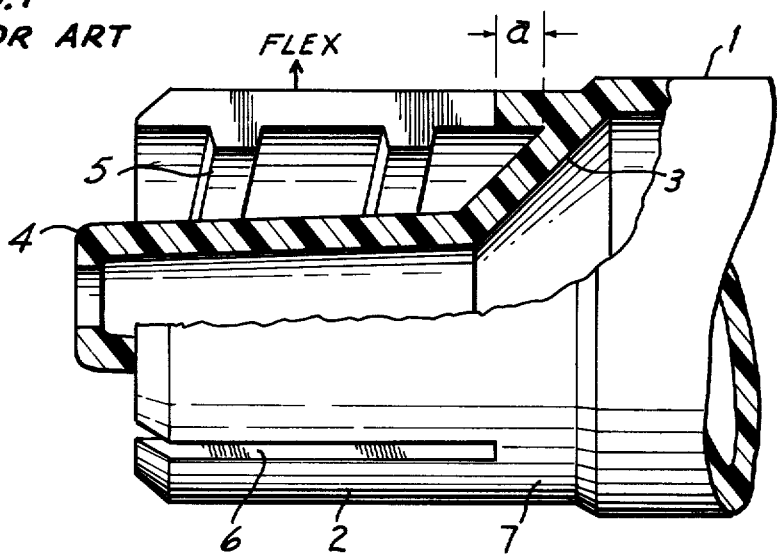
FIG. 1 is a fragmentary view, partially in section, of a forward end of a prior art syringe barrel with integral locking sleeve.

The prior art syringe in FIG. 1 has a thermoplastic barrel 1 with a locking sleeve 2 integrally formed with a front wall 3 of the barrel. The locking sleeve 2 surrounds a tapered needle adapter 4 and includes internal threads 5 for locking to laterally protruding ears of a hypodermic needle hub (not shown). A plurality of slots 6 extend rearwardly from a front end of sleeve 2 to a circumferentially uninterrupted ring portion 7 at a juncture between the sleeve and front wall 3 of the barrel. Circumferentially uninterrupted ring 7 is shown in U.S. Pat. No. 4,027,669, as well as in a co-pending patent application entitled "Syringe Locking Sleeve," Ser. No. 953,607, filed Oct. 23, 1978. The drawings of this co-pending application, as well as those in the above mentioned patent, were taken from engineering drawings of the assignee of the present application. The uninterrupted ring portion protruded a distance "a", as shown in FIG. 1, and was approximately 0.100 inch. This uninterrupted ring 7 was believed to be important as a backup reinforcing to prevent overflexing of the sleeve 2 during use, and thus failure of the threads 5 to hold the hypodermic needle.

Figure 2:
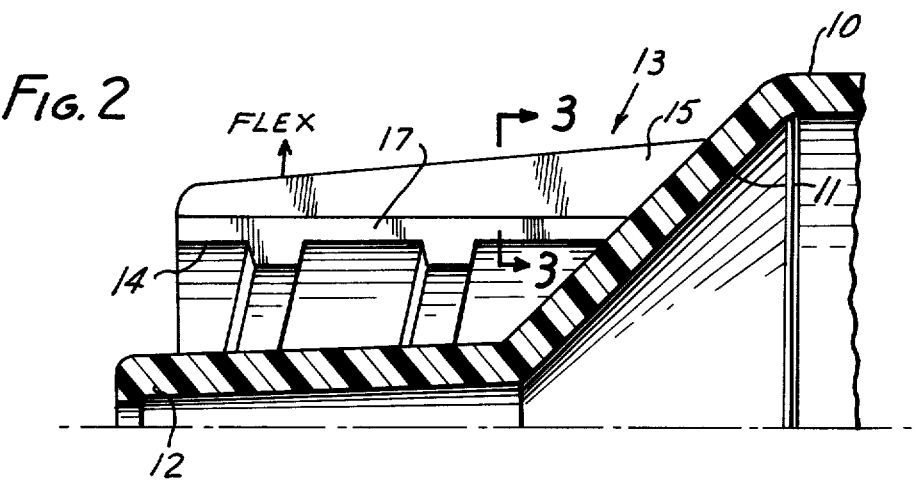
FIG. 2 is a fragmentary sectional view of the locking sleeve of the present invention.
Figure 3:
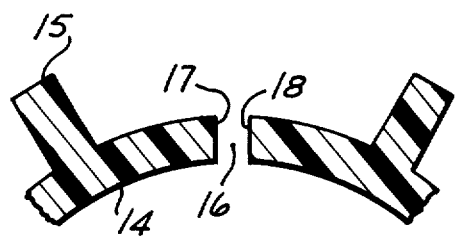
FIG. 3 is an enlarged view taken along line 3—3 of FIG. 2.

FIG. 2 shows the present invention with syringe barrel 10 having a front wall 11 which joins to tapered adapter 12. The locking sleeve shown generally at 13 includes a wall 14 having a thickness of 0.030 to 0.045 inch and radially spaced longitudinally extending flex ribs 15 extending along and integral with an exterior of wall 14. The construction and function of the flex ribs 15 is explained in more detail in the above co-pending Akhavi application. As shown in FIG. 3, a slot 16 is defined by adjacent surfaces 17 and 18.

In FIG. 2, surface 17 is shown extending completely along the entire length of the sleeve to barrel wall 11. Thus, in FIG. 2 there is no backup uninterrupted ring as in 7 of FIG. 1. Preferably, the uninterrupted ring is completely eliminated, but substantial reduction of its length to 0.050 inch or less when combined with the wall thickness dimension and ribs explained above improves moldability and performance of the syringe during use.

To emphasize the critical importance of seemingly very minor structural changes in strip ejected locking sleeves that are longitudinally pulled from their molds without an unscrewing motion, compare the syringe locking sleeve of the above Akhavi co-pending application and the sleeve structure of the instant application. The syringe in the co-pending application has approximately 20 inch-ounce of torque retention holding power on a hypodermic syringe needle. The locking sleeve construction of the present invention has approximately 50% greater holding power of 30 inch-ounce on the same hypodermic needle. Both needles were of the standard two eared type. Both syringes have very fast mold cycle times.

The syringe with integral locking sleeve described above works very well when molded of a polypropylene thermoplastic material. Other thermoplastic material with suitable properties might also be used.

In the foregoing description, a specific example has been used to illustrate the invention. However, it is understood by those skilled in the art that certain modifications can be made to this example without departing from the spirit and scope of the invention.

I claim:

1. A thermoplastic syringe barrel with a front wall integrally joined to a circumferentially interrupted locking sleeve with internal threads, wherein the improvement comprises: said sleeve having at least one slot that extends to within 0.050 inch of the barrel's front wall to enhance mold release flexing of the sleeve for axial strip ejection from a mold during formation and firm locking control during use.

2. A syringe barrel as set forth in claim 1, wherein the slot extends to the barrel's front wall.

3. A syringe barrel as set forth in claim 1, wherein there are a plurality of slots.

4. A syringe barrel as set forth in claim 1, wherein the sleeve has a flexible wall and there is at least one upstanding longitudinal rib extending along an external surface of the sleeve's wall.

5. A syringe barrel as set forth in claim 1, wherein the wall is from 0.030 to 0.045 inch thick.

6. A syringe barrel as set forth in claim 1, wherein the retaining sleeve can withstand approximately 30 inch-ounce torqued on a standard two eared needle hub before losing a grip on such hub.

7. A medical device with a front wall integrally joined to a circumferentially interrupted locking sleeve with internal threads, wherein the improvement comprises: said sleeve having at least one slot that extends to within 0.050 inch of the device's front wall to enhance mold release flexing of the sleeve for axial strip ejection from a mold during formation and firm locking control during use.

* * * * *